(12) United States Patent
Ai et al.

(10) Patent No.: US 11,793,838 B2
(45) Date of Patent: Oct. 24, 2023

(54) STENTING-FREE PHARMACEUTICAL COMPOSITION FOR TREATMENT OF CARDIOVASCULAR AND CEREBROVASCULAR DISEASE

(71) Applicant: Yueyang Traditional Chinese Medicine Hospital, Yueyang (CN)

(72) Inventors: Jinchang Ai, Yueyang (CN); Wu Tang, Yueyang (CN)

(73) Assignee: Yueyang Traditional Chinese Medicine Hospital, Yueyang (JP)

( * ) Notice: Subject to any disclaimer, the term of this patent is extended or adjusted under 35 U.S.C. 154(b) by 0 days.

(21) Appl. No.: 17/320,194

(22) Filed: May 13, 2021

(65) Prior Publication Data

US 2022/0362307 A1   Nov. 17, 2022

(51) Int. Cl.

| | | |
|---|---|---|
| *A61K 35/62* | (2006.01) | |
| *A61K 36/258* | (2006.01) | |
| *A61K 36/537* | (2006.01) | |
| *A61K 36/236* | (2006.01) | |
| *A61K 36/8988* | (2006.01) | |
| *A61P 9/10* | (2006.01) | |
| *A61K 36/88* | (2006.01) | |
| *A61K 36/28* | (2006.01) | |
| *A61K 36/16* | (2006.01) | |
| *A61K 36/484* | (2006.01) | |
| *A61K 36/734* | (2006.01) | |

(52) U.S. Cl.
CPC .............. *A61K 35/62* (2013.01); *A61K 36/16* (2013.01); *A61K 36/236* (2013.01); *A61K 36/258* (2013.01); *A61K 36/28* (2013.01); *A61K 36/484* (2013.01); *A61K 36/537* (2013.01); *A61K 36/734* (2013.01); *A61K 36/88* (2013.01); *A61K 36/8988* (2013.01); *A61P 9/10* (2018.01)

(58) Field of Classification Search
None
See application file for complete search history.

(56) References Cited

PUBLICATIONS

CN111544547A (English translation provided by Google Patents) (Year: 2020).*
CN109200201A, translation provided by Google Patents. (Year: 2019).*

* cited by examiner

*Primary Examiner* — Michael Barker
(74) *Attorney, Agent, or Firm* — NIELDS, LEMACK & FRAME, LLC

(57) ABSTRACT

The present disclosure provides a traditional Chinese medicine (TCM) composition for the treatment of cardiovascular and cerebrovascular diseases and use thereof, and belongs to the technical field of TCM. The composition for the treatment of cardiovascular and cerebrovascular diseases provided by the present disclosure includes the following raw materials: Radix Panacis Quinquefolii, Pheretima, Radix et Rhizoma Salviae Miltiorrhizae, Hirudo, Rhizoma Ligustici Chuanxiong, Rhizoma Gastrodiae, Fructus Crataegi, Stigma Croci, Herba Erigerontis, Semen Ginkgo, and Radix et Rhizoma Glycyrrhizae. The present disclosure treats the cardiovascular and cerebrovascular diseases through treatment based on syndrome differentiation and overall regulation in TCM; with less side effects, excellent efficacy, and fast acting, the present disclosure can achieve a stenting-free effect on the cardiovascular and cerebrovascular diseases.

16 Claims, No Drawings

STENTING-FREE PHARMACEUTICAL COMPOSITION FOR TREATMENT OF CARDIOVASCULAR AND CEREBROVASCULAR DISEASE

TECHNICAL FIELD

The present disclosure relates to the technical field of traditional Chinese medicine (TCM), and in particular to a TCM composition for the treatment of cardiovascular and cerebrovascular diseases and use thereof.

BACKGROUND

Cardiovascular and cerebrovascular diseases collectively refer to diseases in cardiac and cerebral vessels, and generally refer to ischemic or hemorrhagic diseases developed in the heart, brain, and systemic tissues, caused by hyperlipidemia, viscous blood, atherosclerosis, and hypertension. The cardiovascular and cerebrovascular diseases are common diseases that seriously threaten the health of human being, especially the middle-aged and elderly people aged over 50 years, featuring high prevalence rate, disability rate, and mortality; even if the most advanced and sophisticated treatment means are used at present, more than 50% of cerebrovascular accident survivors may still be unable to take care of themselves completely; 15 million people die of cardiovascular and cerebrovascular diseases worldwide every year, which is the leading cause of death.

So far, there are a variety of medicaments for the treatment of cardiovascular and cerebrovascular diseases on sale, of which there are mainly vasodilators, hypotensors, and platelet agglutination inhibitors in TCM and western medicine; however, pharmaceutical chemicals have more side effects, and long-term use thereof may do harm to human blood vessels and organs. The existing TCM has shortcomings of slow acting and long administration time.

SUMMARY

In view of this, an objective of the present disclosure is to provide a TCM composition with less side effects, excellent efficacy, and fast acting.

To achieve the above objective, the present disclosure provides the following technical solutions:

The present disclosure provides a TCM composition for the treatment of cardiovascular and cerebrovascular diseases, including the following raw materials: Radix Panacis Quinquefolii, Pheretima, Radix et Rhizoma Salviae Miltiorrhizae, Hirudo, Rhizoma Ligustici Chuanxiong, Rhizoma Gastrodiae, Fructus Crataegi, Stigma Croci, Herba Erigerontis, Semen Ginkgo, and Radix et Rhizoma Glycyrrhizae.

Preferably, the raw materials may have the following parts by weight: 2-4 parts by weight of Radix Panacis Quinquefolii, 5-15 parts by weight of Pheretima, 10-20 parts by weight of Radix et Rhizoma Salviae Miltiorrhizae, 10-20 parts by weight of Hirudo, 10-20 parts by weight of Rhizoma Ligustici Chuanxiong, 5-15 parts by weight of Rhizoma Gastrodiae, 10-20 parts by weight of Fructus Crataegi, 1-2 parts by weight of Stigma Croci, 5-20 parts by weight of Herba Erigerontis, 1-5 parts by weight of Semen Ginkgo, and 1-5 parts by weight of Radix et Rhizoma Glycyrrhizae.

Preferably, the raw materials may have the following parts by weight: 2-4 parts by weight of Radix Panacis Quinquefolii, 8-12 parts by weight of Pheretima, 12-18 parts by weight of Radix et Rhizoma Salviae Miltiorrhizae, 12-18 parts by weight of Hirudo, 12-18 parts by weight of Rhizoma Ligustici Chuanxiong, 7-13 parts by weight of Rhizoma Gastrodiae, 13-17 parts by weight of Fructus Crataegi, 1-2 parts by weight of Stigma Croci, 12-18 parts by weight of Herba Erigerontis, 2-4 parts by weight of Semen Ginkgo, and 2-4 parts by weight of Radix et Rhizoma Glycyrrhizae.

Preferably, the raw materials may have the following parts by weight: 3 parts by weight of Radix Panacis Quinquefolii, 10 parts by weight of Pheretima, 10 parts by weight of Radix et Rhizoma Notoginseng, 15 parts by weight of Radix et Rhizoma Salviae Miltiorrhizae, 15 parts by weight of Hirudo, 15 parts by weight of Rhizoma Ligustici Chuanxiong, 10 parts by weight of Rhizoma Gastrodiae, 15 parts by weight of Fructus Crataegi, 1 part by weight of Stigma Croci, 15 parts by weight of Herba Erigerontis, 3 parts by weight of Semen Ginkgo, and 3 parts by weight of Radix et Rhizoma Glycyrrhizae.

Preferably, the Hirudo may be sun-dried Hirudo.
Preferably, the Pheretima may be dried Pheretima.
The present disclosure further provides a medicament for the treatment of cardiovascular and cerebrovascular diseases, where the above TCM composition is prepared into a decoction, a powder, a pill, or a capsule.

The present disclosure further provides use of the above TCM composition or the above medicament for the treatment of cardiovascular and cerebrovascular diseases.

Preferably, the cardiovascular and cerebrovascular diseases may include hypertension, coronary heart disease, stroke, and hyperlipidemia.

In the TCM composition for the treatment of cardiovascular and cerebrovascular diseases provided by the present disclosure, Radix Panacis Quinquefolii, Hirudo, Pheretima, Rhizoma Gastrodiae, and Semen Ginkgo, serving as sovereign drugs, may be compatibly combined to boost qi, free the network vessels, and relieve spasm by calming endogenous wind; Radix et Rhizoma Notoginseng, Radix et Rhizoma Salviae Miltiorrhizae, Stigma Croci, and Fructus Crataegi, serving as ministerial drugs, may be compatibly combined to promote blood circulation for removing blood stasis; Rhizoma Ligustici Chuanxiong, Radix et Rhizoma Glycyrrhizae, and Herba Erigerontis, serving as adjuvant drugs, may be compatibly combined to activate qi and promote blood circulation to arrest pain. All drugs may be administered compatibly to boost qi, free the network vessels, relieve spasm by calming endogenous wind, promote blood circulation for removing blood stasis, and activate qi to arrest pain.

Each drug has the following actions:

Radix Panacis Quinquefolii: Invigorate qi and nourish yin; clear heat to lessen fire; invigorate the spleen and moisten the lung; supplement the true origin.

Dried Pheretima: Clear heat for calming endogenous wind; free the channels and quicken the network vessels.

Radix et Rhizoma Notoginseng: Promote blood circulation for hemostasis, and disperse swelling and relieve pain. Modern pharmacological studies have found that Radix et Rhizoma Notoginseng plays roles in dilating blood vessels, improving microcirculation disturbance, reducing myocardial oxygen consumption, inhibiting platelet aggregation, prolonging the coagulation time, reducing blood lipids, and scavenging free radicals, with anti-inflammatory and antioxidant activity.

Radix et Rhizoma Salviae Miltiorrhizae: Promote blood circulation for removing blood stasis; free the channels to arrest pain; clear the heart and eliminate vexation; cool the blood and disperse welling-abscesses. Modern medical experiments have demonstrated that Radix et Rhizoma Salviae Miltiorrhizae plays roles in lowering blood pressure, dilating the coronary artery, improving myocardial ischemia, inhibiting platelet aggregation, and reducing blood viscosity, with hypoglycemic and antimicrobial activity.

Hirudo: Hirudo mainly expels malign blood, blood stasis, and menostasis and breaks blood to eliminate aggregation.

Rhizoma Ligustici Chuanxiong: Belonging to liver and gallbladder channels, Rhizoma Ligustici Chuanxiong is acrid and sweet in taste and warm in nature. The drug mainly activates qi to expel stagnation, dispels pathogenic wind and removes dampness, and promotes blood circulation to arrest pain.

Rhizoma Gastrodiae: Relieve spasm by calming endogenous wind; repress the liver yang; dispel pathogenic wind and free the network vessels. Rhizoma Gastrodiae extract plays roles in lowering blood pressure, reducing the resistance of peripheral, cerebral, and coronary vessels, and slowing heart rate, with analgesic and anti-inflammatory activity.

Fructus Crataegi: Fructus Crataegi has lipid-lowering, antihypertensive, cardiotonic, and anti-arrythmic effects.

Stigma Croci: Belonging to heart and liver channels, Stigma Croci is slightly bitter in taste and warm in nature. Stigma Croci promotes blood circulation and frees the channels, and dissipates stasis to arrest pain, being effective in treating menostasis, dysmenorrhea, lochiometra, chest stuffiness and pains, abdominal pain caused by stasis, stabbing chest and rib-side pain, knocks and falls, and painful swelling caused by sores and boils.

Herba Erigerontis: Dissipate cold and resolve the exterior; promote blood circulation and soothe the sinews; arrest pain; disperse accumulations.

Semen Ginkgo: Astringe lung qi, stabilize panting and treat cough, check turbid vaginal discharge, and reduce urination; Semen Ginkgo contents may reduce serum cholesterol levels, increase phospholipids, improve C/P ratio, and have a certain antihypertensive effect on hypertensives.

Radix et Rhizoma Glycyrrhizae: Belonging to heart, lung, spleen, and stomach channels, Radix et Rhizoma Glycyrrhizae clears heat and resolves toxin, moistens the lung and suppresses cough, and harmonizes all drugs.

The present disclosure has the following beneficial effects:

The TCM composition of the present disclosure may achieve functions of boosting qi, freeing the network vessels, relieving spasm by calming endogenous wind, promoting blood circulation and removing blood stasis, and activating qi to arrest pain; the TCM composition may be effective in treating cardiovascular and cerebrovascular diseases, with less side effects, excellent efficacy, and fast acting; moreover, patients with cardiovascular and cerebrovascular diseases who require stenting may achieve a stenting-free effect after oral administration of the TCM composition of the present disclosure.

DETAILED DESCRIPTION

The present disclosure provides a TCM composition for the treatment of cardiovascular and cerebrovascular diseases, including the following raw materials: Radix Panacis Quinquefolii, Pheretima, Radix et Rhizoma Salviae Miltiorrhizae, Hirudo, Rhizoma Ligustici Chuanxiong, Rhizoma Gastrodiae, Fructus Crataegi, Stigma Croci, Herba Erigerontis, Semen Ginkgo, and Radix et Rhizoma Glycyrrhizae. Preferably, the raw materials may have the following parts by weight: 2-4 parts by weight of Radix Panacis Quinquefolii, 5-15 parts by weight of Pheretima, 10-20 parts by weight of Radix et Rhizoma Salviae Miltiorrhizae, 10-20 parts by weight of Hirudo, 10-20 parts by weight of Rhizoma Ligustici Chuanxiong, 5-15 parts by weight of Rhizoma Gastrodiae, 10-20 parts by weight of Fructus Crataegi, 1-2 parts by weight of Stigma Croci, 5-20 parts by weight of Herba Erigerontis, 1-5 parts by weight of Semen Ginkgo, and 1-5 parts by weight of Radix et Rhizoma Glycyrrhizae. More preferably, the raw materials may have the following parts by weight: 2-4 parts by weight of Radix Panacis Quinquefolii, 8-12 parts by weight of Pheretima, 12-18 parts by weight of Radix et Rhizoma Salviae Miltiorrhizae, 12-18 parts by weight of Hirudo, 12-18 parts by weight of Rhizoma Ligustici Chuanxiong, 7-13 parts by weight of Rhizoma Gastrodiae, 13-17 parts by weight of Fructus Crataegi, 1-2 parts by weight of Stigma Croci, 12-18 parts by weight of Herba Erigerontis, 2-4 parts by weight of Semen Ginkgo, and 2-4 parts by weight of Radix et Rhizoma Glycyrrhizae. Most preferably, the raw materials may have the following parts by weight: 3 parts by weight of Radix Panacis Quinquefolii, 10 parts by weight of Pheretima, 10 parts by weight of Radix et Rhizoma Notoginseng, 15 parts by weight of Radix et Rhizoma Salviae Miltiorrhizae, 15 parts by weight of Hirudo, 15 parts by weight of Rhizoma Ligustici Chuanxiong, 10 parts by weight of Rhizoma Gastrodiae, 15 parts by weight of Fructus Crataegi, 1 part by weight of Stigma Croci, 15 parts by weight of Herba Erigerontis, 3 parts by weight of Semen Ginkgo, and 3 parts by weight of Radix et Rhizoma Glycyrrhizae.

Sources of all drugs are not particularly limited in the present disclosure, and commercially available products conventional in the art can be used. In preferred examples of the present disclosure, the Stigma Croci may preferably be from Tibet, the Rhizoma Gastrodiae and the Radix et Rhizoma Notoginseng may preferably be from Yunnan, and the Herba Erigerontis may preferably be from Xinjiang. The type of the Hirudo is not particularly limited in the present disclosure, and sun-dried Hirudo may preferably be used. The type of the Pheretima is not particularly limited in the present disclosure, and dried Pheretima may preferably be used; the drying method of the Pheretima is not particularly limited in the present disclosure, as long as all drying methods conventional in the art may be used.

In the TCM composition for the treatment of cardiovascular and cerebrovascular diseases provided by the present disclosure, Radix Panacis Quinquefolii, Hirudo, Pheretima, Rhizoma Gastrodiae, and Semen Ginkgo, serving as sovereign drugs, may be compatibly combined to boost qi, free the network vessels, and relieve spasm by calming endogenous wind; Radix et Rhizoma Notoginseng, Radix et Rhizoma Salviae Miltiorrhizae, Stigma Croci, and Fructus Crataegi, serving as ministerial drugs, may be compatibly combined to promote blood circulation for removing blood stasis; Rhizoma Ligustici Chuanxiong, Radix et Rhizoma Glycyrrhizae, and Herba Erigerontis, serving as adjuvant drugs, may be compatibly combined to activate qi and promote blood circulation to arrest pain. All drugs may be compatibly combined to boost qi, free the network vessels, relieve spasm by calming endogenous wind, promote blood circulation and remove blood stasis, and activate qi to arrest pain, jointly achieving a therapeutic effect on cardiovascular and cerebrovascular diseases; moreover, with less side effects effect, excellent efficacy, and fast acting, patients with cardiovascular and cerebrovascular diseases who require stenting may achieve a stenting-free effect after oral administration of the TCM composition of the present disclosure.

The present disclosure further provides a medicament for the treatment of cardiovascular and cerebrovascular diseases, where the above TCM composition is prepared into a decoction, a powder, a pill, or a capsule.

Preparation methods of the decoction, the powder, the pill, or the capsule are not particularly limited in the present disclosure, as long as conventional preparation methods of the decoction, the powder, the pill, or the capsule in the art may be used. Preferably, when the decoction is prepared, the following steps may be included: accurately weighing all parts by weight of raw materials, adding five times the total weigh of water, decocting with strong fire for 30 min.

The present disclosure further provides use of the above TCM composition or the above medicament for the treatment of cardiovascular and cerebrovascular diseases.

The types of the cardiovascular and cerebrovascular diseases are not particularly limited in the present disclosure, and hypertension, coronary heart disease, stroke, and hyperlipidemia may preferably be included. When patients with cardiovascular and cerebrovascular diseases take the TCM composition of the present disclosure, administration method may be as follows: when the TCM composition is a decoction, take 300-500 ml every morning and night, respectively; when the TCM composition is a powder, take 1-5 g with warm water every morning, noon, and night, respectively.

The technical solutions of the present disclosure will be described in detail below in conjunction with examples, but they should not be construed as limiting the protection scope of the present disclosure.

Example 1

3 g of Radix Panacis Quinquefolii, 10 g of dried Pheretima, 15 g of Radix et Rhizoma Salviae Miltiorrhizae, 15 g of sun-dried Hirudo, 15 g of Rhizoma Ligustici Chuanxiong, 10 g of Rhizoma Gastrodiae, 15 g of Fructus Crataegi, 1 g of Stigma Croci, 15 g of Herba Erigerontis, 3 g of Semen Ginkgo, and 3 g of Radix et Rhizoma Glycyrrhizae were included.

Example 2

4 g of Radix Panacis Quinquefolii, 5 g of Pheretima, 10 g of Radix et Rhizoma Salviae Miltiorrhizae, 10 g of Hirudo, 10 g of Rhizoma Ligustici Chuanxiong, 5 g of Rhizoma Gastrodiae, 10 g of Fructus Crataegi, 1 g of Stigma Croci, 10 g of Herba Erigerontis, 1 g of Semen Ginkgo, and 1 g of Radix et Rhizoma Glycyrrhizae were included.

Example 3

4 g of Radix Panacis Quinquefolii, 15 g of Pheretima, 20 g of Radix et Rhizoma Salviae Miltiorrhizae, 20 g of Hirudo, 20 g of Rhizoma Ligustici Chuanxiong, 15 g of Rhizoma Gastrodiae, 20 g of Fructus Crataegi, 1 g of Stigma Croci, 20 g of Herba Erigerontis, 5 g of Semen Ginkgo, and 5 g of Radix et Rhizoma Glycyrrhizae were included.

Example 4

4 g of Radix Panacis Quinquefolii, 8 g of dried Pheretima, 12 g of Radix et Rhizoma Salviae Miltiorrhizae, 12 g of sun-dried Hirudo, 12 g of Rhizoma Ligustici Chuanxiong, 7 g of Rhizoma Gastrodiae, 13 g of Fructus Crataegi, 2 g of Stigma Croci, 12 g of Herba Erigerontis, 2 g of Semen Ginkgo, and 2 g of Radix et Rhizoma Glycyrrhizae were included.

Example 5

2 g of Radix Panacis Quinquefolii, 12 g of dried Pheretima, 18 g of Radix et Rhizoma Salviae Miltiorrhizae, 18 g of sun-dried Hirudo, 18 g of Rhizoma Ligustici Chuanxiong, 13 g of Rhizoma Gastrodiae, 17 g of Fructus Crataegi, 2 g of Stigma Croci, 18 g of Herba Erigerontis, 4 g of Semen Ginkgo, and 4 g of Radix et Rhizoma Glycyrrhizae were included.

Example 6

The TCM composition of the present disclosure features scientific composition, reasonable compatibility, and safe administration. To demonstrate the therapeutic effect of the TCM composition of the present disclosure, the present disclosure selected and provided clinical observation data for 100 related patients; the 100 patients were randomized into two groups: treatment group (n=52) and control group (n=48); there was no statistical significance in disease condition and basic personal information between both groups of patients, and there was comparability between both groups.

Selection criteria: A hundred patients with stable angina pectoris of coronary heart disease were selected.

Diagnostic criteria: Angina pectoris is clinically manifested as episodic chest pain, which mainly occurs in the superior or middle segment of the corpus sterni, spreads to the precordial region within a palm-sized range, and even traverses the anterior chest with an unclear boundary. The chest pain often radiates to the left shoulder, from the left medial arm to the ring finger and the little finger, or to the neck, the pharynx, or the mandible. The chest pain is often crushing, oppressive, or tension-type; the pain may also have a burning sensation, but is not sharp, unlike stabbing or prickling pain, occasionally with a fear of dying. Once the angina pectoris attacks, patients usually stop their original activities unconsciously until symptoms are relieved. The attack is evoked by mechanical labor or emotional excitation (such as rage, anxiety, and superexcitation), and satiety, cold, smoking, tachycardia, and shock may be inducing factors. The pain attacks during labor or excitement, rather than after a very hard day. Typical angina pectoris often attacks under similar conditions. But sometimes, the same labor only causes angina pectoris in the morning, rather than in the afternoon, suggesting that there is a correlation with a low pain threshold in the morning. The pain usually worsens progressively after occurrence and then disappears gradually within 3-5 min, which usually remits after original symptom-induced activities are stopped. The pain also remits within minutes after sublingual administration of nitroglycerin. The pain may attack every few days or weeks or several times a day.

According to typical characteristics and signs of the attack, the angina pectoris may remit after rest or sublingual administration of nitroglycerin. Considering age and other risk factors of coronary heart disease present, angina pectoris caused by other diseases may be ruled out.

Implementation solution: As required, the treatment group was given 300-500 ml of a decoction prepared from the TCM composition of the present disclosure every morning and night. A month was one course of treatment. Statistics was performed after one course of treatment.

The control group was given Yindan Xinnaotong Ruanjiaonang (soft capsules) orally according to drug instructions. A month was one course of treatment. Statistics was performed after one course of treatment.

The results were as follows:

In the treatment group, 30 (57.7%) patients were improved, 12 (23.1%) were effective, and 9 (17.3%) were ineffective, with a total response rate of 80.8%; in the control group, 17 patients (35.4%) were improved, 12 (25%) were effective, and 19 (39%) were ineffective, with a total response rate of 60.4%. The condition that personal feelings, instrumental diagnosis, and TCM diagnosis results of patients were improved compared with those before treatment was defined as improved; the condition that patients' conditions were controlled was defined as effective; the condition that symptoms were ineffective and there was no significant improvement was defined as ineffective.

From observation results, the TCM composition of the present disclosure had an excellent therapeutic effect on patients with stable angina pectoris of coronary heart disease. Herein, four critically ill patients with cardiovascular and cerebrovascular diseases were diagnosed in western medicine to have to delay disease progression by means of stenting; after administration of the TCM composition in Example 1, cardiovascular and cerebrovascular diseases were improved remarkably without stenting, and finally, the patients were successfully cured.

The TCM composition of the present disclosure was prepared into other dosage forms, and identical or similar results were obtained in experiments. Examples are not listed in detail herein to prevent repetition. Furthermore, what is claimed in the present disclosure is a TCM composition, rather than a dose form or a preparation method. Therefore, any dose forms prepared from the TCM composition of the present disclosure and medicaments for the treatment of similar diseases shall fall within the protection scope of the present disclosure.

The above descriptions are merely preferred implementations of the present disclosure. It should be noted that a person of ordinary skill in the art may further make several improvements and modifications without departing from the principle of the present disclosure, and such improvements and modifications should be deemed as falling within the protection scope of the present disclosure.

What is claimed is:

1. A traditional Chinese medicine (TCM) composition for the treatment of cardiovascular and cerebrovascular diseases, comprising the following raw materials: Radix Panacis Quinquefolii, Pheretima, Radix et Rhizoma Salviae Miltiorrhizae, Hirudo, Rhizoma Ligustici Chuanxiong, Rhizoma Gastrodiae, Fructus Crataegi, Stigma Croci, Herba Erigerontis, Semen Ginkgo, and Radix et Rhizoma Glycyrrhizae, wherein the TCM composition is in the form of a pill or a capsule.

2. The TCM composition according to claim 1, wherein the raw materials have the following parts by weight: 2-4 parts by weight of Radix Panacis Quinquefolii, 5-15 parts by weight of Pheretima, 10-20 parts by weight of Radix et Rhizoma Salviae Miltiorrhizae, 10-20 parts by weight of Hirudo, 10-20 parts by weight of Rhizoma Ligustici Chuanxiong, 5-15 parts by weight of Rhizoma Gastrodiae, 10-20 parts by weight of Fructus Crataegi, 1-2 parts by weight of Stigma Croci, 5-20 parts by weight of Herba Erigerontis, 1-5 parts by weight of Semen Ginkgo, and 1-5 parts by weight of Radix et Rhizoma Glycyrrhizae.

3. The TCM composition according to claim 2, wherein the raw materials have the following parts by weight: 2-4 parts by weight of Radix Panacis Quinquefolii, 8-12 parts by weight of Pheretima, 12-18 parts by weight of Radix et Rhizoma Salviae Miltiorrhizae, 12-18 parts by weight of Hirudo, 12-18 parts by weight of Rhizoma Ligustici Chuanxiong, 7-13 parts by weight of Rhizoma Gastrodiae, 13-17 parts by weight of Fructus Crataegi, 1-2 parts by weight of Stigma Croci, 12-18 parts by weight of Herba Erigerontis, 2-4 parts by weight of Semen Ginkgo, and 2-4 parts by weight of Radix et Rhizoma Glycyrrhizae.

4. The TCM composition according to claim 2, wherein the raw materials have the following parts by weight: 3 parts by weight of Radix Panacis Quinquefolii, 10 parts by weight of Pheretima, 10 parts by weight of Radix et Rhizoma Notoginseng, 15 parts by weight of Radix et Rhizoma Salviae Miltiorrhizae, 15 parts by weight of Hirudo, 15 parts by weight of Rhizoma Ligustici Chuanxiong, 10 parts by weight of Rhizoma Gastrodiae, 15 parts by weight of Fructus Crataegi, 1 part by weight of Stigma Croci, 15 parts by weight of Herba Erigerontis, 3 parts by weight of Semen Ginkgo, and 3 parts by weight of Radix et Rhizoma Glycyrrhizae.

5. The TCM composition according to claim 1, wherein the Hirudo is sun-dried Hirudo.

6. The TCM composition according to claim 2, wherein the Hirudo is sun-dried Hirudo.

7. The TCM composition according to claim 3, wherein the Hirudo is sun-dried Hirudo.

8. The TCM composition according to claim 4, wherein the Hirudo is sun-dried Hirudo.

9. The TCM composition according to claim 1, wherein the Pheretima is dried Pheretima.

10. The TCM composition according to claim 2, wherein the Pheretima is dried Pheretima.

11. The TCM composition according to claim 3, wherein the Pheretima is dried Pheretima.

12. The TCM composition according to claim 4, wherein the Pheretima is dried Pheretima.

13. A method for treating cardiovascular and cerebrovascular diseases, comprising administering the TCM composition according to claim 1 to a subject in need thereof.

14. The method according to claim 13, wherein the raw materials have the following parts by weight: 2-4 parts by weight of Radix Panacis Quinquefolii, 5-15 parts by weight of Pheretima, 10-20 parts by weight of Radix et Rhizoma Salviae Miltiorrhizae, 10-20 parts by weight of Hirudo, 10-20 parts by weight of Rhizoma Ligustici Chuanxiong, 5-15 parts by weight of Rhizoma Gastrodiae, 10-20 parts by weight of Fructus Crataegi, 1-2 parts by weight of Stigma Croci, 5-20 parts by weight of Herba Erigerontis, 1-5 parts by weight of Semen Ginkgo, and 1-5 parts by weight of Radix et Rhizoma Glycyrrhizae.

15. The method according to claim 13, wherein the raw materials have the following parts by weight: 2-4 parts by weight of Radix Panacis Quinquefolii, 8-12 parts by weight of Pheretima, 12-18 parts by weight of Radix et Rhizoma Salviae Miltiorrhizae, 12-18 parts by weight of Hirudo, 12-18 parts by weight of Rhizoma Ligustici Chuanxiong, 7-13 parts by weight of Rhizoma Gastrodiae, 13-17 parts by weight of Fructus Crataegi, 1-2 parts by weight of Stigma Croci, 12-18 parts by weight of Herba Erigerontis, 2-4 parts by weight of Semen Ginkgo, and 2-4 parts by weight of Radix et Rhizoma Glycyrrhizae.

16. The method according to claim 13, wherein the cardiovascular and cerebrovascular diseases comprise hypertension, coronary heart disease, stroke, and hyperlipidemia.

* * * * *

UNITED STATES PATENT AND TRADEMARK OFFICE
CERTIFICATE OF CORRECTION

| | | |
|---|---|---|
| PATENT NO. | : 11,793,838 B2 | Page 1 of 1 |
| APPLICATION NO. | : 17/320194 | |
| DATED | : October 24, 2023 | |
| INVENTOR(S) | : Jinchang Ai and Wu Tang | |

It is certified that error appears in the above-identified patent and that said Letters Patent is hereby corrected as shown below:

On the Title Page

Item (73), should read as follows:
-- Assignee: Yueyang Traditional Chinese Medicine Hospital, Yueyang City, (CN) --

Signed and Sealed this
Twenty-fourth Day of September, 2024

Katherine Kelly Vidal
*Director of the United States Patent and Trademark Office*